US006063924A

United States Patent [19]

Hall-Goulle

[11] Patent Number: 6,063,924

[45] Date of Patent: *May 16, 2000

[54] SOLUBLE CHROMOPHORES CONTAINING SOLUBILISING GROUPS WHICH CAN BE EASILY REMOVED

[75] Inventor: Véronique Hall-Goulle, Bern, Switzerland

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/681,204

[22] Filed: Jul. 22, 1996

[30] Foreign Application Priority Data

| | | | |
|---|---|---|---|
| Jul. 28, 1995 | [CH] | Switzerland | 2222-95 |
| Oct. 19, 1995 | [CH] | Switzerland | 2968-95 |

[51] Int. Cl.[7] ..................... C07D 471/04; C07D 487/22; C09B 67/50

[52] U.S. Cl. ........................... 546/49; 534/790; 540/122; 540/135; 540/136; 544/99; 544/296; 544/300; 544/380; 546/36; 546/41; 546/56; 546/57; 548/457; 548/471; 548/479; 548/482; 552/213

[58] Field of Search ................................... 548/453, 457, 548/471, 479, 482; 546/256, 276.7, 49, 56, 36, 41, 57; 544/296, 333, 99, 300, 380; 540/122, 135, 136; 534/618, 624, 634, 732, 733, 790; 552/213

[56] References Cited

U.S. PATENT DOCUMENTS

| | | | |
|---|---|---|---|
| 2,831,850 | 4/1958 | Merian et al. | 260/207 |
| 4,666,455 | 5/1987 | Jost et al. | 8/506 |
| 4,791,204 | 12/1988 | Jost et al. | 548/101 |
| 5,484,943 | 1/1996 | Zambounis et al. | 548/453 |
| 5,518,539 | 5/1996 | Hao et al. | 106/495 |
| 5,527,922 | 6/1996 | Zambounis etal. | 548/453 |
| 5,561,232 | 10/1996 | Hao et al. | 546/14 |
| 5,723,626 | 3/1998 | Hao et al. | 548/467 |

FOREIGN PATENT DOCUMENTS

| | | |
|---|---|---|
| 0648770 | 4/1995 | European Pat. Off. . |
| 0648817 | 4/1995 | European Pat. Off. . |
| 648817 | 4/1995 | European Pat. Off. . |
| 718697 | 6/1996 | European Pat. Off. . |

*Primary Examiner*—Richard L. Raymond
*Assistant Examiner*—Deepak Rao
*Attorney, Agent, or Firm*—Kevin T. Mansfield; David R. Crichton

[57] ABSTRACT

Compounds of formula $$A(B)_x \quad (I),$$

wherein x is an integer from 1 to 4,

A is the radical of a chromophore of the quinacridone, anthraquinone, perylene, indigo, quinophthalone, isoindolinone, isoindoline, dioxazine, phthalocyanine, diketopyrrolopyrrole or azo series, which radical A contains x N-atoms linked with B, preferably with at least one immediately adjacent or conjugated carbonyl group.

B is a group of formula

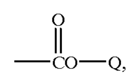

and, if x=2, 3 or 4, can also be one, two or three hydrogen atom(s), and wherein Q is a group of formula

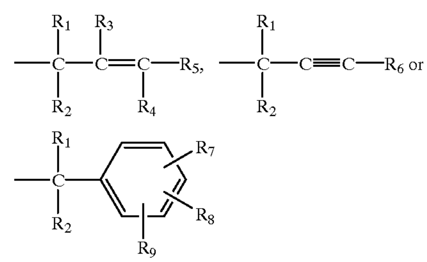

These soluble chromophores can be readily converted to the corresponding pigments by heating, even in the substrate into which they can be incorporated without any difficulty in dissolved form.

$R_1$–$R_9$ are as defined herein.

9 Claims, No Drawings

SOLUBLE CHROMOPHORES CONTAINING SOLUBILISING GROUPS WHICH CAN BE EASILY REMOVED

The present invention relates to novel soluble chromophores containing unsaturated hydrocarbyloxycarbonyl groups which can be easily removed. Because of this property, said chromophores can be readily converted into the corresponding pigments even in the substrate into which they can be incorporated without any difficulty in dissolved form.

Soluble chromophores which contain carbamate groups are known from EP-A 648 770 and 648 817, which chromophores can be converted into the corresponding pigments by heating to elevated temperature with consequent removal of the hydrocarbyloxycarbonyl groups which form the carbamate groups. Among numerous other radicals, generic mention is also made of alkenylcarbamate groups.

Very surprisingly, it has now been found that soluble chromophores containing unsaturated carbamate radicals in β-position to the oxygen of the carbonyloxy group can be converted at markedly lower temperature, i.e. with a considerably lower expenditure of energy, than the closest known soluble carbamate groups-contaning chromophores which do not have this feature.

Accordingly, the invention relates to compounds of formula $A(B)_x$ (I), wherein x is an integer from 1 to 4, A is the radical of a chromophore of the quinacridone, anthraquinone, perylene, indigo, quinophthalone, isoindolinone, isoindoline, dioxazine, phthalocyanine, diketopyrrolopyrrole or azo series, which radical A contains x N-atoms linked to B, preferably with at least one directly adjacent or conjugated carbonyl group, B is a group of formula

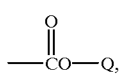

and, if x=2, 3 or 4, can also be one, two or three hydrogen atom(s), and wherein Q is a group of formula

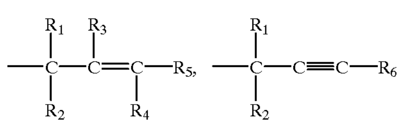 or

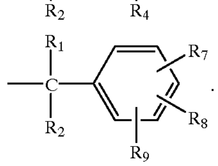

$R_1$ and $R_2$ are each independently of the other hydrogen, $C_1$–$C_{24}$alkyl; $C_1$–$C_{24}$alkyl, $C_3$–$C_{24}$alkenyl, $C_3$–$C_{24}$alkynyl, $C_4$–$C_{12}$cycloalkyl, $C_4$–$C_{12}$cycloalkenyl, each of which is interrupted by O, S or $N(R_9)_2$; phenyl or biphenyl, each of which is unsubstituted or substituted by $C_1$–$C_6$alkyl, $C_1$–$C_6$alkoxy, halogen, cyano or nitro, $R_3$, $R_4$ and $R_5$ are each independently of one another hydrogen, $C_1$–$C_{24}$alkyl or $C_3$–$C_{24}$alkenyl, $R_6$ is hydrogen, $C_1$–$C_{24}$alkyl, $C_3$–$C_{24}$alkenyl or a group of formula

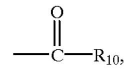, 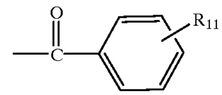 or

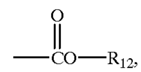

$R_7$ and $R_8$ are each independently of the other hydrogen, $C_1$–$C_6$alkyl, $C_1$–$C_6$alkoxy, halogen, cyano, nitro, $N(R_9)_2$, phenyl which is unsubstituted or substituted by halogen, cyano, nitro, $C_1$–$C_6$alkyl or $C_1$–$C_6$alkoxy, $R_9$ and $R_{10}$ are $C_1$–$C_6$alkyl, $R_{11}$ is hydrogen or $C_1$–$C_6$alkyl, and $R_{12}$ is hydrogen, $C_1$–$C_6$alkyl, unsubstituted or $C_1$–$C_6$alkyl-substituted phenyl.

A is the radical of known chromophores having the basic structure $A(H)_x$, for example

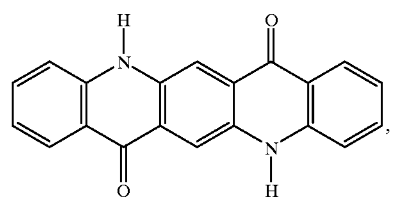,

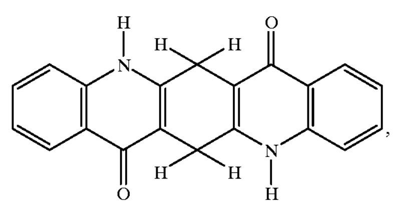,

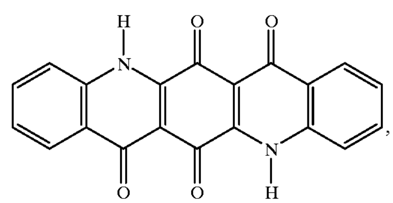,

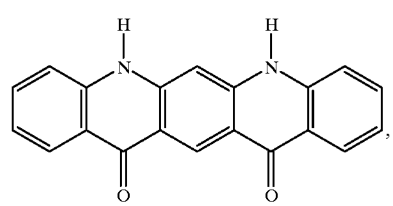,

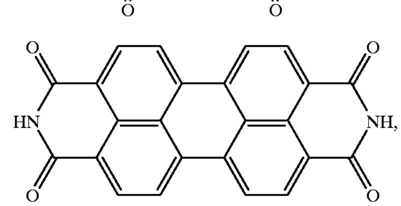

-continued
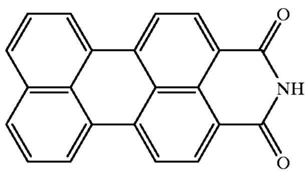
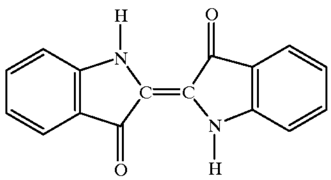
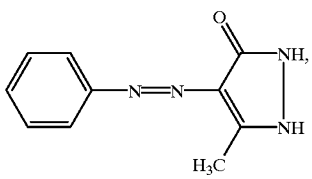
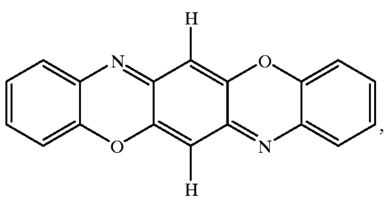
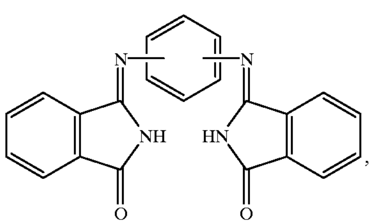
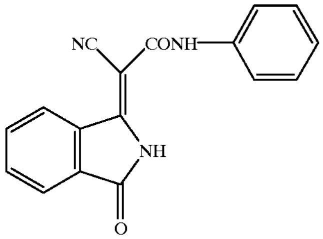
-continued
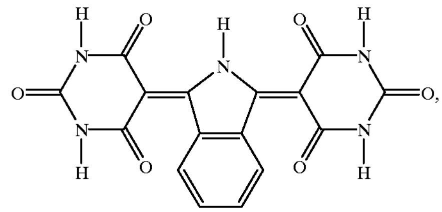
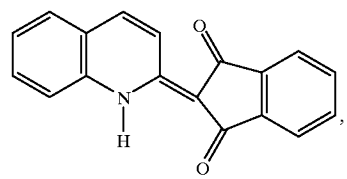
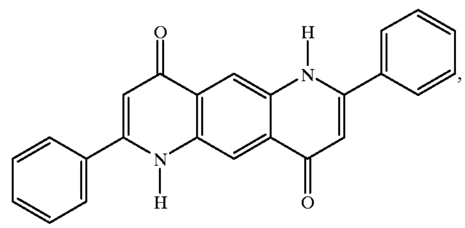
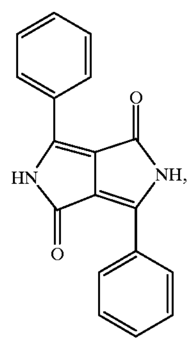
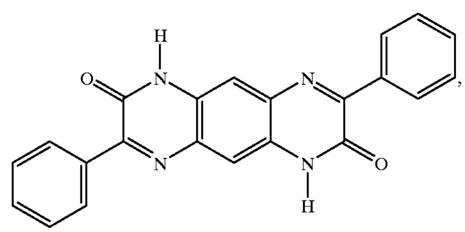
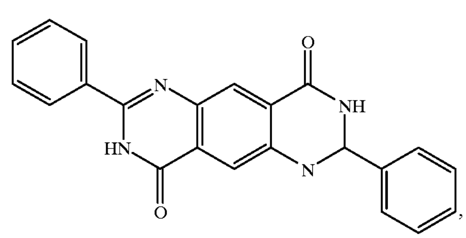

-continued

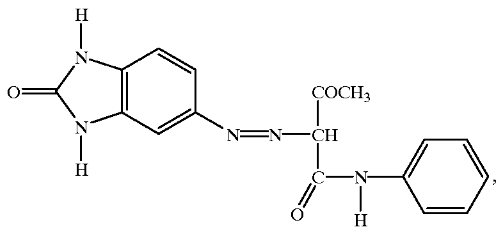,

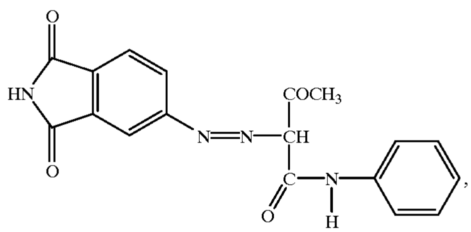,

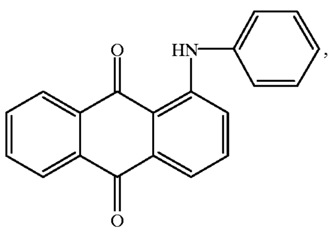,

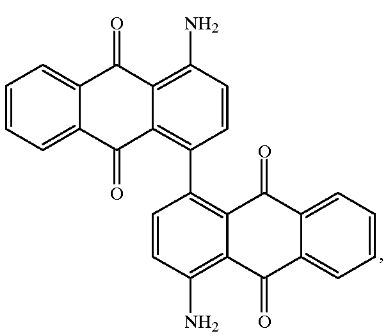,

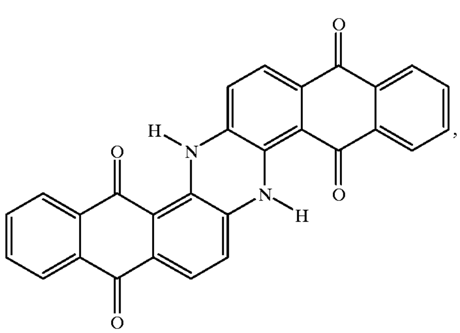,

-continued

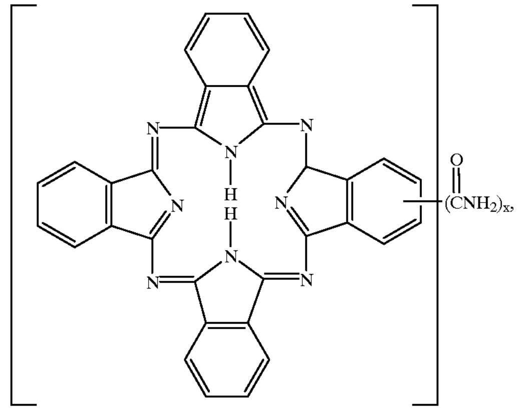

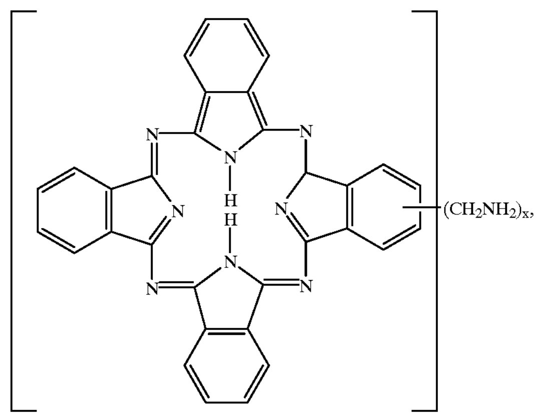

and all known derivatives thereof.

$C_1$–$C_6$Alkyl substituents are typically methyl, ethyl, n-propyl, isopropyl, n-butyl, sec-butyl, tert-butyl, n-pentyl, tert-amyl, n-hexyl, or 2,2-dimetylbutyl. $C_1$–$C_{24}$Alkyl can additionally be, for example, n-octyl, 1,1,3,3-tetramethylbutyl, 2-ethylhexyl, nonyl, decyl, dodecyl, tetradecyl, hexadecyl, octadecyl, eicosyl, heneicosyl, docosyl or tetracoxyl.

$C_3$–$C_{24}$Alkenyl is $C_3$–$C_{24}$alkyl which is mono- or polyunsaturated and where two or more than two double bonds can be isolated or conjugated, for example allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or the different isomers of hexenyl, octenyl, nonenyl, decenyl, dodecenyl, tetradecenyl, hexadecenyl, octadecenyl, eicosenyl, heneicosenyl, docosenyl, tetracosenyl, hexadienyl, octadienyl, nonadienyl, decadienyl, dodecadienyl, tetradecadienyl, hexadecadienyl, octadecadienyl, eicosadienyl, heneicosadienyl, docosadienyl or tetracosadienyl.

$C_4$–$C_{12}$Cycloalkyl is, for example, a monocyclic cycloalkyl, typically cyclobutyl, cyclopentyl, cyclohexyl, trimethylcyclohexyl or menthyl, or a polycyclic cycloalkyl, typically thujyl, bornyl, 1-adamantyl or 2-adamantyl.

$C_4$–$C_{12}$Cycloalkenyl is $C_4$–$C_{12}$cycloalkyl which is mono- or polyunsatured and where two or more than two double bonds can be isolated or conjugated, typically 2-cyclobuten- 1-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbomadien-1-yl or 7,7-dimethyl-2,4-norcaradien-3-yl.

$C_3$–$C_{24}$Alkynyl is $C_3$–$C_{24}$alkyl or $C_3$–$C_{24}$alkenyl, each of which is once or more than once doubly unsaturated and wherein the triple bonds can be isolated or conjugatedamong themselves or with double bonds, typically 1-propin-3-yl, 1-butin-4-yl, 1-pentin-5-yl, 2-methyl-3-butin-2-yl, 1,4-pentadiin-3-yl, 1,3-pentadiin-5-yl, 1-hexin-6-yl, cis-3-methyl-2-penten-4-in-1-yl, trans-3-methyl-2-penten-4-in-1-yl, 1,3-hexadiin-5-yl, 1-octin-8-yl, 1-nonin-9-yl, 1-decin-10-yl or 1-tetracosin-24-yl.

$C_1$–$C_6$Alkoxy is typically methoxy, ethoxy, n-propoxy, isopropoxy, n-butoxy, tert-butoxy, n-amyloxy, tert-amyloxy or n-hexyloxy.

Halogen is typically iodo, fluoro, bromo or, preferably, chloro.

Particularly interesting compounds are those of formula I, wherein $R_1$ is $C_1$–$C_{24}$alkyl, $C_3$–$C_{24}$alkenyl, $C_3$–$C_{24}$alkynyl, phenyl which is unsubstituted or substituted by $C_1$–$C_6$alkyl, $C_1$–$C_6$alkoxy, halogen, cyano or nitro, and $R_6$ is $C_1$–$C_{24}$alkyl or $C_3$–$C_{24}$alkenyl, in particular those compounds of formula I, wherein $R_1$ and $R_2$ are methyl, $R_3$, $R_4$ and $R_5$ are each independently of one another hydrogen or $C_1$–$C_{12}$alkyl, $R_6$ is $C_1$–$C_6$alkyl, and $R_7$ and $R_8$ are each independently of the other hydrogen, $C_1$–$C_6$alkyl, $C_1$–$C_6$alkoxy, halogen, cyano, nitro, $N(R_9)_2$ or phenyl, and, very particularly, those compounds of formula I, wherein B is a group of formula

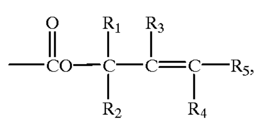

$R_1$ and $R_2$ are methyl, and $R_3$, $R_4$ and $R_5$ are each independently of one another hydrogen or $C_1$–$C_{12}$alkyl.

Preferred compounds of formula I are:

a) perylenecarboximides of formula (IIa)

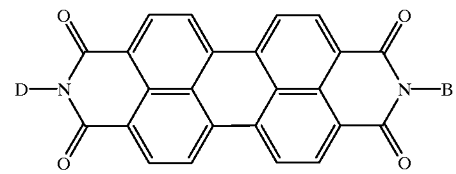

or (IIb)

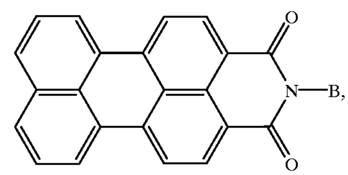

wherein D is hydrogen, $C_1$–$C_6$alkyl; unsubstituted or halogen- or C–$C_6$alkyl-substituted phenyl, benzyl or phenethyl, or B, b) quinacridones of formula (III)

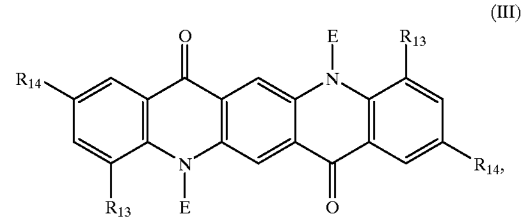

wherein $R_{13}$ and $R_{14}$ are each independently of the other hydrogen, halogen, $C_1$–$C_{24}$alkyl, $C_1$–$C_6$alkoxy or phenyl, c) dioazines of formula (IV)

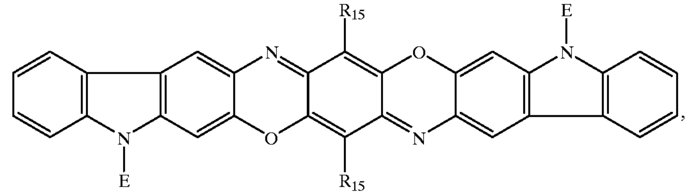

wherein $R_{15}$ is hydrogen, halogen or $C_1$–$C_{24}$alkyl, or of formula (IVa)

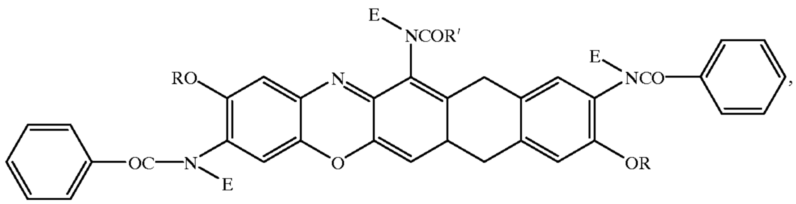

wherein R and R' are each independently of the other $C_1$–$C_4$alkyl, d) islindolines of formulae (V)

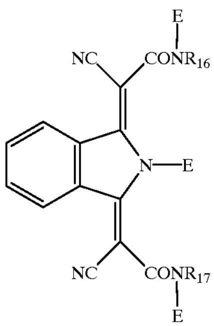

, (VI)

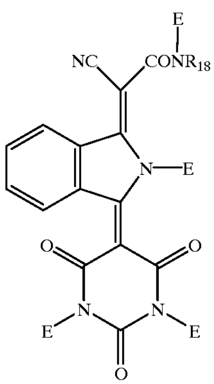

or (VII)

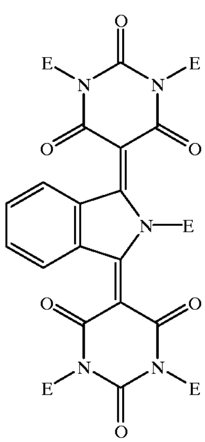

, wherein $R_{16}$ is a group of formula

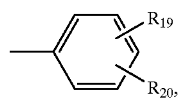

$R_{17}$ is hydrogen, $C_1$–$C_{24}$alkyl, benzyl or a group of formula

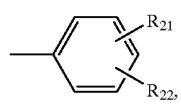

$R_{18}$ has the same meaning as $R_{16}$, $R_{19}$, $R_{20}$, $R_{21}$ and $R_{22}$ are each independently of one another hydrogen, $C_1$–$C_{24}$alkyl, $C_1$–$C_6$alkoxy, halogen or trifluoromethyl, e) indigo derivatives of formula (VIII)

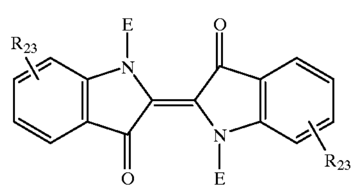

, wherein $R_{23}$ is hydrogen, CN, $C_1$–$C_6$alkyl, $C_1$–$C_6$alkoxy or halogen, f) azobenzimidazolones of formula (IX)
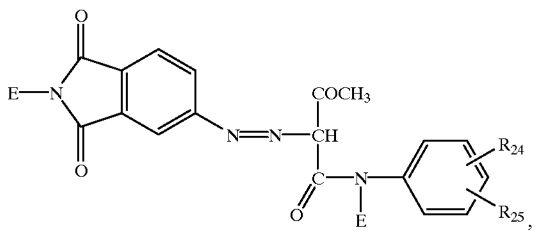
wherein $R_{24}$ and $R_{25}$ are each independently of the other hydrogen, halogen, $C_1$–$C_6$alkyl or $C_1$–$C_6$alkoxy,
g) anthraquinoid compounds of formula
(X)
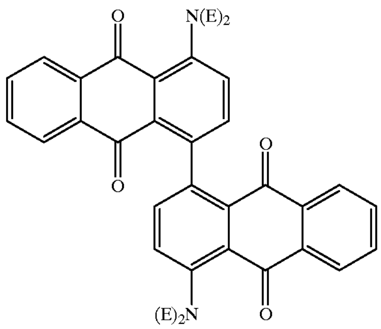
-continued
or
(XI)
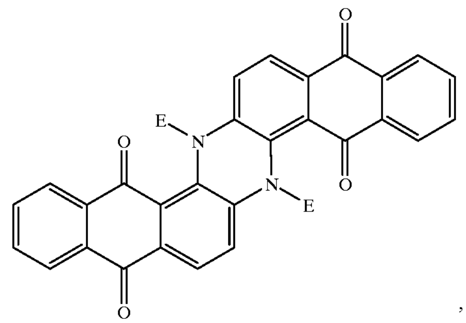
,
h) phthalocyanines of formula
(XII)
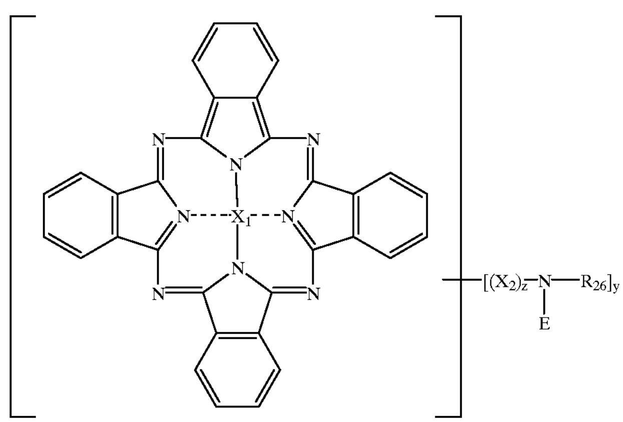
, wherein $X_1$ is $H_2$, a divalent metal selected from the group consisting of Cu(II), Zn(II), Fe(II), Ni(II), Ru(II), Rh(II), Pd(II), Pt(II), Mn(II), Mg(II), Be(II), Ca(II), Ba(II), Cd(II), Hg(II), Sn(II), Co(II) and Pb(II), preferably Cu(II), Zn(II), Fe(II) Ni(II) or Pd(II), or a divalent oxo metal selected from the group consisting of V(O), Mn(O) and TiO, $X_2$ is —CH($R_{24}$)—, —CO— or —$SO_2$—, $R_{26}$ is hydrogen, $C_1$–$C_6$alkyl, —N(E)$R_{27}$, —-NHCO$R_{28}$. —CO$R_{28}$ or

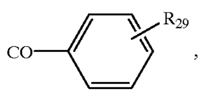

, $R_{27}$ is hydrogen or $C_1$–$C_6$alkyl, $R_{28}$ is $C_1$–$C_6$alkyl, and $R_{29}$ is hydrogen, halogen, $C_1$–$C_6$alkyl or $C_1$–$C_6$alkoxy, z is 0 or 1, and y is an integer from 1 to 4, i) isoindolinones of formula

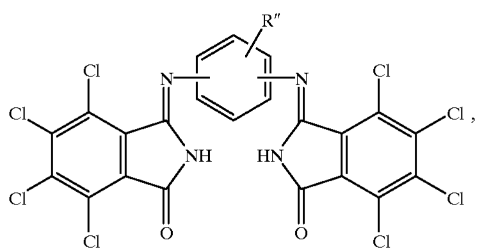

wherein R" is hydrogen or $C_1$–$C_4$alkyl, and j) pyrrolo[3,4-c]pyrroles of formula (XIII)

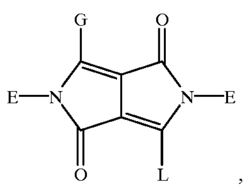

, wherein G and L are each independently of the other a group of formula

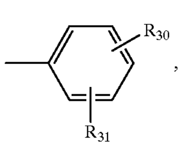

,

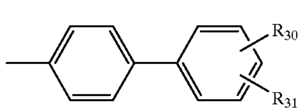

,

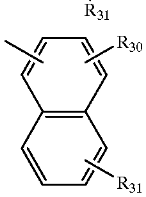

,

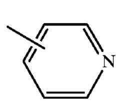

,

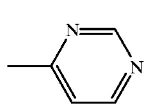

,

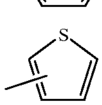

,

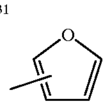

or

-continued

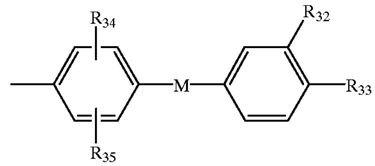

, wherein $R_{30}$ and $R_{31}$ are each independently of the other hydrogen, halogen, $C_1$–$C_{24}$alkyl, $C_1$–$C_6$alkoxy, $C_1$–$C_{18}$alkylmercapto, $C_1$–$C_{18}$alkylamino, —CN, —$NO_2$, phenyl, trifluoromethyl, $C_5$–$C_6$cycloalkyl, —C═N—($C_1$–$C_{24}$alkyl),

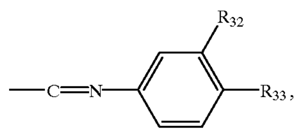

, imidazolyl, pyrrazolyl, triazolyl, piperazinyl, pyrrolyl, oxazolyl, benzoxazolyl, benzthiazolyl, benzimidazolyl, morpholinyl, piperidinyl or pyrrolidinyl, M is —$CH_2$—, —CH($CH_3$)—, —C$(CH_3)_2$—, —CH═N—, —N═N—, —O—, —S—, —SO—, —$SO_2$— or —N$R_{36}$—, $R_{32}$ and $R_{33}$ are each independently of the other hydrogen, halogen, $C_1$–$C_6$alkyl, $C_1$–$C_6$alkoxy or —CN, $R_{34}$ and $R_{35}$ are each independently of the other hydrogen, halogen or $C_1$–$C_6$alkyl, and $R_{36}$ is hydrogen or $C_1$–$C_6$alkyl, E in the above formulae being hydrogen or B, with the proviso that E in each formula is at least once B, and B has the meaning stated above to which the above preferences apply.

$R_{30}$ and $R_{31}$ in formula XIII defined as $C_1$–$C_{18}$alkylmercapto are typically methylmercapto, ethylmercapto, propylmercapto, butylmercapto, octylmercapto, decylmercapto, hexydecylmercapto or octadecylmercapto, and defined as $C_1$–$C_{18}$alkylamino are typically methylamino, ethylamino, propylamino, hexylamino, decylamino or octadecylamino.

Particularly preferred are quinacridones of formula III, wherein $R_{13}$ and $R_{14}$ are each independently of the other hydrogen, chloro or methyl, or pyrrolo[3,4-c]pyrroles of formula XIII, wherein G and L are identical and are a group of formula

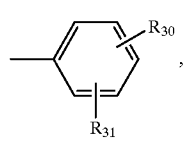

,

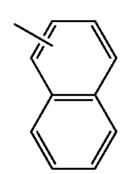

,

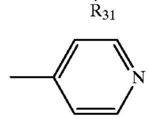

,

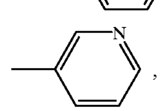

, or

-continued

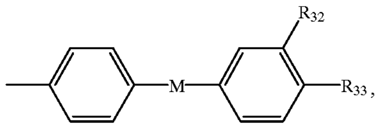

wherein $R_{30}$ and $R_{31}$ are each independently of the other hydrogen, chloro, bromo, $C_1$–$C_4$alkyl, $C_1$–$C_6$alkoxy, $C_1$–$C_6$alkylamino, CN or phenyl, M is —O—, —$NR_{36}$—, —N═N— or —$SO_2$—, $R_{32}$ and $R_{33}$ are hydrogen, and $R_{36}$ is hydrogen, methyl or ethyl, or anthraquinoid compounds of formula XI, wherein E in formulae III, XIII and XI has the meaning stated above.

Particularly preferred are quinacridones of formula (XIV)

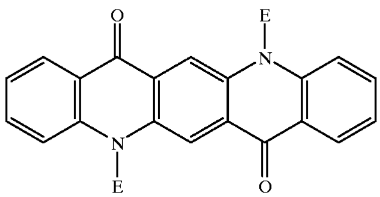

or (XV)

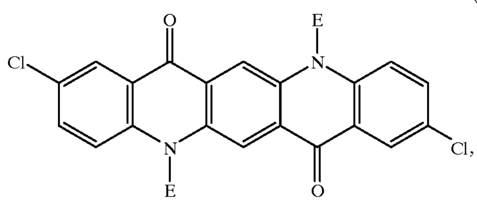

wherein E is hydrogen or B, with the proviso that E in each formula is at least once B, and B has the meaning stated above, pyrrolopyrroles of formula (XVI)

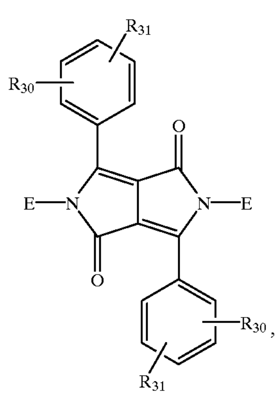

wherein $R_{30}$ and $R_{31}$ are each independently of the other hydrogen, methyl, tert-butyl, chloro, bromo, CN or phenyl, and E is hydrogen or B, with the proviso that E is at least once B, and B has the meaning stated above, and anthraquinoid compounds of formula (XI)

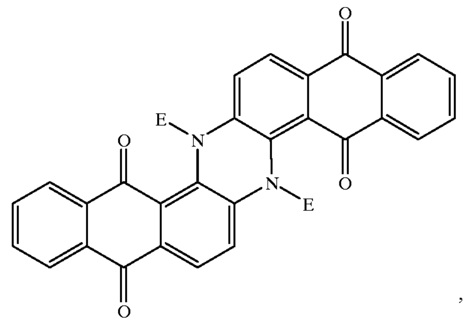

wherein E is hydrogen or B, with the proviso that E is at least once B, and B has the meaning stated above.

The compounds of formula I can be prepared in general analogy to methods known per se, such as those disclosed in EP-A 648 770 and EP-A 648 817, typically by reacting a compound of formula $A(H)_x$, (XVII), wherein A and x have the meanings stated above, in the desired molar ratio with a dicarbonate of formula

B—O—B (XVIII), or with a trihaloacetate of formula $(R_{37})_3C$—B (XIX), or with an azide of formula $BN_3$ (XX), or with a carbonate of formula

—$OR_{38}$ (XXI), or with an alkylidene-iminooxyformate of formula (XXII)

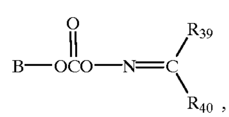

wherein B in each case has the meaning stated above, $R_{37}$ is chloro, fluoro or bromo, $R_{38}$ is $C_1$–$C_4$alkyl, or phenyl which is unsubstituted or substituted by halogen, $C_1$–$C_4$alkyl, $C_1$–$C_4$alkoxy or —CN, $R_{39}$ is —CN or —$COOR_{38}$, and $R_{40}$ is phenyl which is unsubstituted or substituted by halogen, $C_1$–$C_4$alkyl, $C_1$–$C_4$alkoxy or —CN, in an aprotic organic solvent in the presence of a base as catalyst, conveniently in the temperature range from 0 to 120° C., preferably from 10 to 100° C., over 2 to 80 hours.

The compound of formula XVII is preferably reacted with a dicarbonate of formula XVIII.

The compounds of formula XVII, the dicarbonates of formula XVIII, the trihaloacetates of formula XIX, the azides of formula XX, the carbonates of formula XXI and the alkylideneiminooxyformates of formula XXII are known substances. However, any that are novel may be prepared in general accordance with commonly known methods.

The molar ratio between the compound of formula XVII and the compounds of formulae XVIII–XXII depends on x, i.e. on the number of radicals B to be introduced. However, the compounds of formulae XVIII–XXII are conveniently used in 2- to 10-fold excess.

Suitable aprotic organic solvents are typically ethers, such as tetrahydrofuran or dioxane, or glycol ethers such as ethylene glycol methyl ether, ethylene glycol ethyl ether, diethylene glycol monomethyl ether or diethylene glycol monoethyl ether, and also dipolar aprotic solvents, typically acetonitrile, benzonitrile, N,N-dimethylformamide, N,N-dimethylacetamide, nitrobenzene, N-methylpyrrolidone, halogenated aliphatic or aromatic hydrocarbons, e.g. trichloroethane, benzene or alkyl-, alkoxy- or halogen-substituted benzene, such as toluene, xylene, anisol or chlorobenzene, or aromatic N-heterocycles, such as pyridine, picoline or quinoline. Preferred solvents are typically tetrahydrofuran, N,N-dimethylformamide, N-methylpyrrolidone. The indicated solvents can also be used as mixtures. It is expedient to use 5–20 parts by weight of solvent per 1 part by weight of the reactants.

Bases suitable as catalysts are typically the alkali metals themselves, such as lithium, sodium or potassium as well as the hydroxides and carbonates thereof, or alkali metal amides, such as lithium amide, sodium amide or potassium amide, or alkali metal hydrides, such as lithium hydride, sodium hydride or potassium hydride, or alkaline earth metal alcoholates or alkali metal alcoholates, which are derived in particular from primary, secondary or tertiary aliphatic alcohols containing 1 to 10 carbon atoms, typically lithium, sodium or potassium methylate, ethylate, n-propylate, isopropylate, n-butylate, sec-butylate, tert-butylate, 2-methyl-2-butylate, 2-methyl-2-pentylate, 3-methyl-3-pentylate, 3-ethyl-3-pentylate, and also organic aliphatic, aromatic or heterocyclic N-bases, including e.g. diazabicyclooctene, diazabicycloundecene and 4-dimethylaminopyridine, and trialkylamines such as trimethylamine or triethylamine. A mixture of these bases may also be used.

The organic N-bases are preferred, typically diazabicyclooctane, diazabicycloundecene and, preferably, 4-dimethylaminopyridine.

The reaction is conveniently carried out in the temperature range from 10 to 100° C., preferably from 18 to 40° C., i.e. preferably at room temperature, and under atmospheric pressure.

Dicarbonates of formula

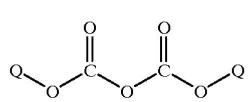

which are suitable for the preparation of the novel compounds of formula I can also be prepared in accordance with a novel method which is the object of a parallel application, by reacting at least one ester carbonate of formula (XXIII)

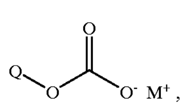

wherein Q has the meaning stated above, $M^+$ is $Na^+$, $Li^+$, $K^+$ or $NR_{41}R_{42}R_{43}R_{44}^+$, and $R_{41}$ to $R_{44}$ are each independently of one another hydrogen, $C_1$–$C_{18}$alkyl, $C_5$–$C_{10}$cycloalkyl or $C_7$–$C_{18}$aralkyl, with 40–50 mol % of a sulfochloride of formula (XXIV)

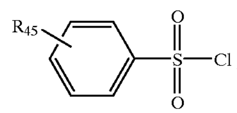

wherein $R_{45}$ is —H, —$CH_3$, —$CH_2CH_3$, —Cl, —Br, —$OCH_3$ or —$NO_2$, in the presence of 0.8–5 mol % of a catalyst of formula (XXV)

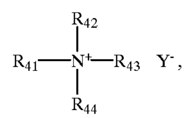

wherein $R_{41}$ to $R_{44}$ have the meaning given above, and $Y^-$ is a non-nucleophilic anion, and 1–5 mol % of a heterocyclic aromatic amine in an nonpolar inert solvent, all molar amounts being based on 100 mol % of ester carbonate of formula XXIII, in the temperature range from −10° C. to +25° C.

$R_{41}$–$R_{44}$ $C_1$–$C_{18}$alkyl is typically methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-octyl, 1,1,3,3-tetra-methylbutyl, 2-ethylhexyl, nonyl, decyl, dodecyl, tetradecyl, hexadecyl or octadecyl.

$C_4$–$C_{12}$Cycloalkyl is, for example, a monocyclic cycloalkyl, typically cyclobutyl, cyclopentyl, cyclohexyl, trimethylcyclohexyl or menthyl, or a polycyclic cycloalkyl, typically thujyl, bornyl, 1-adamantyl or 2-adamantyl.

$C_7$–$C_{18}$Aralkyl is typically 2-benzyl-2-propyl, β-phenylethyl, α,α-dimethylbenzyl, ω-phenyl-butyl, ω-phenyloctyl, ω-phenyldodecyl or 3-methyl-5-(1',1',3',3'-tetramethyl)butylbenzyl. $C_7$–$C_{24}$Aralkyl can additionally also be e.g. 2,4,6-tritert-butylbenzyl or 1-(3,5-dibenzylphenyl)-3-methyl-2-propyl.

Heterocyclic aromatic amines are typically pyridine, α-, β- or γ-picoline, 2,4-, 2,6-, 3,4- or 3,5-lutidine, dollidine or quinoline.

Nonpolar inert solvents are those having a dielectric constant $\epsilon \geqq 10$ and which are immiscible with water and which, under the conditions of this process, react neither with the ester carbonate of formula (XXIII) nor with the sulfochloride of formula (XXIV), for example aromatic hydrocarbons, typically benzene, toluene, xylene, mesitylene or ethylbenzene, aliphatic hydrocarbons, typically pentane, hexane, cyclohexane, heptane, octane, decane or decahydronaphthalene, noncyclic ethers, typically diethyl ether, diisopropyl ether, diisopropyl ether or diisobutyl ether, or mixtures thereof, for example special boiling-point spirit or ®Shell-Sol products.

Sulfochlorides of formula (XXIV) are preferably benzene sulfochloride and p-toluene sulfochloride.

The sulfochloride of formula (XXIV) is particularly preferably p-toluene sulfochloride. Preferred catalyst cations are those wherein $R_2$ to $R_5$ are each independently of one another methyl, ethyl, butyl, benzyl, octyl, dodecyl or octadecyl, in particular those wherein the sum of the carbon atoms in the groups $R_{41}$ to $R_{44}$ is from 10 to 24.

Particularly preferred catalyst cations are those wherein $R_{41}$ to $R_{44}$ are butyl, or $R_{41}$ and $R_{42}$ are methyl, $R_{43}$ is methyl or ethyl, and $R_{44}$ is benzyl, dodecyl or octadecyl.

Non-nucleophilic catalyst anions $Y^-$ are typically $Cl^-$, $Br^-$, $F^-$, $J^-$, $NO_3^-$, $ClO_4^-$, $HSO_4^-$, $PF_6^-$, $B(C_6H_5)_4^-$ or $BF_4^-$.

Catalyst anions are preferably bromide and chloride, in particular chloride.

A particularly preferred catalyst of formula (XXV) is benzyltrimethylammonium chloride.

Heterocyclic aromatic amine is preferably pyridine.

Solvents are preferably aromatic hydrocarbons.

Particularly preferred solvents are toluene and xylene.

The preferred amount of sulfochloride of formula (XXIV) is c. 45 mol %, based on (XXIII).

The preferred amount of catalyst of formula (XXV) is 1.0–1.5 mol %, based on (XXIII).

The preferred amount of heterocyclic aromatic amine is 1–3 mol %, based on (XXIII). The particularly preferred amount of heterocyclic aromatic amine is c. 3 mol %, based on (XXIII).

The amount of solvent is not critical. It is preferred to use exactly the amount of solvent required to make the reaction mixture readily stirrable during the entire reaction, which amount can differ depending on the pyrocarbonic acid diester to be prepared.

The reaction temperature is preferably from 0° C. to +20° C.

The reaction temperature is particularly preferably from 0° C. to +10° C.

The reaction time depends on the amounts of catalyst and heterocyclic aromatic amine as well as on the temperature. The reaction is usually completed after ½ to 100 hours, preferably after ½ to 10 hours.

All the chemicals required are known and are commercially available or can be prepared according to known methods.

The process can be carried out most simply by introducing the solvent and all educts (XXIII) to (XXV) concurrently or in succession in any order into the reaction vessel at the reaction temperature. Conveniently, at least part of the solvent is placed in the reaction vessel first and the sulfochloride is added last.

The novel compounds of formula I are excellently suited as fluorescent pigments for colouring high molecular weight material in the mass. Illustrative examples of suitable high molecular weight organic materials which can be coloured with the novel compounds of formula I are vinyl polymers, typically polystyrene, poly-αmethylstyrene, poly-p-methylstyrene, poly-p-hydroxystyrene, poly-p-hydroxyphenylstyrene, poly(methylacrylate) and poly(acrylamide) as well as the corresponding methacrylic compounds, poly(methylmaleate), poly(acrylonitrile), poly(methacrylonitrile), poly(vinyl chloride), poly(vinyl fluoride), poly(vinylidene chloride), poly(vinylidene fluoride), poly(vinyl acetate), poly(methylvinyl ether) and poly(butylvinyl ether); novolaks derived from $C_1$–$C_6$aldehydes, typically formaldehyde and acetaldehyde, and a binuclear, preferably mononuclear, phenol, which is unsubstituted or substituted by one or two $C_1$–$C_9$alkyl groups, one or two halogen atoms or a phenyl ring, for example o-, m- or p-cresol, xylene, p-tert-butylphenol, o-, m- or p-nonylphenol, p-chlorophenol or p-phenylphenol, or a compound containing more than one phenolic group, typically resorcinol, bis(4-hydroxyphenyl)methane or 2,2-bis(4-hydroxyphenyl)propane; polymers derived from maleinimide and/or maleic anhydride, typically copolymers of maleic anhydride and styrene; poly(vinylpyrrolidone), biopolymers and their derivatives, for example cellulose, starch, chitin, chitosan, gelatin, zein, cellulose ethyl ether, nitrocellulose, cellulose acetate and cellulose butyrate; natural resins and synthetic resins, typically rubber, casein, silicone and silicone resins, ABS, urea/formaldehyde and melamine/formaldehyde resins, alkyd resins, phenolic resins, polyamides, polyimides, polyamide/imides, polysulfones, polyether sulfones, polyphenylene oxides, polyurethanes, polyureas, polycarbonates, polyarylenes, polyarylenesulfides, polyepoxides, polyolefins and polyalkadienes. High molecular weight organic materials are preferably e.g. cellulose ethers and cellulose esters, typically cellulose ethyl ether, nitrocellulose, cellulose acetate or cellulose butyrate, natural resins or synthetic resins, for example polymerisation or condensation resins, typically aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, polyphenylene oxides, rubber, casein, silicone and silicone resins, singly or in mixtures.

The indicated high molecular weight organic compounds can be singly or as mixtures in the form of plastics, melts or in the form of spinning solutions, varnishes, paints or printing inks. Depending on the end use requirement, it is expedient to use the novel compounds of formula I as toners or in the form of preparations.

The novel compounds of formula I are particularly suitable for the mass coloration of polyvinyl chloride and, in particular, of polyolefins, e.g. polyethylene and polypropylene, as well as of paints and also of powder coating compositions, printing inks and coating materials.

The novel compounds of formula I can be used in an amount of 0.01 to 30% by weight, preferably of 0.1 to 10% by weight, based on the high molecular weight organic material to be pigmented.

The pigmenting of the high molecular weight organic materials with the novel compounds of formula I is conveniently effected by incorporating the compound of formula I by itself or in the form of masterbatches in these substrates using roll mills, mixing or milling apparatus. The pigmented material is then brought into the desired final form by methods which are known per se, conveniently by calendering, moulding, extruding, coating, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated into the novel compounds of formula I before or after working the pigments into the polymers. To obtain different shades, it is also possible to add to the high molecular weight organic materials fillers or other chromophoric components such as white, coloured or black pigments in any amount, in addition to the novel compounds.

For pigmenting paints, coating materials and printing inks, the high molecular weight organic materials and the novel compounds of formula I, together with optional additives such as fillers, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

When used for colouring e.g. polyvinyl chloride or polyolefins or in printing inks, the novel compounds of formula I are distinguished by good allround fastness properties, such as good fastness to migration, light and weathering and, in particular, by the unexpectedly high fluorescence.

Of very great importance, however, is the entirely surprising ease with which the soluble chromophores of this invention can be converted to the corresponding pigments of formula $A(H)_x$ even in the substrate into which they have already been incorporated. This can be achieved in the simplest manner by thermal treatment (heating to the temperature range of 50 to 210° C., preferably of 100 to 170° C., depending on the pigment) of the solids, solutions or dispersions containing the novel soluble compounds in organic or aqueous media, polymer solutions or melts. This permits to colour paints, printing inks, in particular for ink jet printing and plastics, also e.g. in fibre form, with properties that are on the whole enhanced, such as purity, colour strength, brilliance and transparency, as well as interesting applications in the analytical field.

Accordingly, the invention also relates to high molecular weight organic material containing in the mass a pigment of formula $A(H)_x$ produced in situ by thermal degradation of a soluble compound of formula I, as well as to thermosensitive, photosensitive or chemosensitive recording material and also to photo- or electroluminescent materials containing a novel compound of formula I.

It has even been found that in the case of specific compounds of formula I the thermal treatment by heating to the temperature range from 100 to 180° C., preferably from 105 to 120° C., can result in crystal modification conversions of the corresponding chromophores XVII.

The invention therefore additionally also relates to a process for the crystal modification conversion of chromophores of formula XVII by reacting them to compounds of formula I, typically according to the process indicated above, as well as to the thermal treatment of the resulting compounds of formula I in the temperature range from 100 to 180° C.

The following Examples illustrate the invention in more detail.

A) Preparation of the Dicarbonates

EXAMPLE A1

A solution of 84.1 g (1 mol) of 2-methyl-3-butin-2-ol in 1.75 I of toluene is cooled to 3° C. and 40 g (1 mol) of 60% sodium hydride are added in increments in an inert gas atmosphere, such that the temperature does not rise above 10° C. After the addition of 250 ml of toluene, the mixture is stirred overnight at 18° C. The brown solution is cooled to 5° C., and 101.7 g (2.3 mol) of $CO_2$ are then introduced at 5–10° C. The reaction mixture is heated to 18° C. and then 3.2 g (0.014 mol) of benzyltrimethylammonium chloride, 2.4 g (0.03 mol) of pyridine and 82.8 g (0.43 mol) of toluene-4-sulfochloride are added in succession. The resulting suspension is stirred for three days at room temperature. 260 ml of 5% aqueous $H_2SO_4$ are added at 5° C., such that the temperature does not rise above 10° C. The organic phase is isolated, washed with 5×400 ml of water, dried over $Na_2SO_4$ and concentrated under vacuum. The crude product (94.8 g) is treated with hexane, affording 70 g (59% of theory, calculated on the basis of the toluene-4-sulfochloride), of a pure white di(2-methyl-3-butin-2-yl) dicarbonate having an m.p of 102.8° C.

| Analysis: | C | H |
|---|---|---|
| calcd.: | 60.50% | 5.92% |
| found: | 60.41% | 6.16% |

EXAMPLE A2

Example A1 is repeated, but starting from 2-methyl-3-buten-2-ol instead of from 2-methyl-3-butin-2-ol, and using 0.50 mol of toluene-4-sulfochloride instead of 0.40 mol of toluene-4-sulfochloride. Di(2-methyl-3-buten-2-yl) dicarbonate of good quality is obtained in yield of 61% of theory (calculated on the basis of the toluene-4-sulfochloride). Analysis: $^1$H-NMR ($CDCl_3$: 6.08 (dd 2H); 5.29 (d, 2H); 5.19 (d, 2H); 1.60 (s, 12H)

EXAMPLE A3

Example A1 is repeated, but starting from 3-methyl-2-buten-1-ol instead of from 2-methyl-3-butin-2-ol, giving di(3-methyl-2-buten-1-yl)dicarbonate having a $^1$H-NMR spectrum which is well in keeping with expectations. Analysis: $^1$H-NMR ($CDCl_3$): 5.38 (m, 2H); 4.73 (d, 4H); 1.77 (s, $—CH_3$); 1.73 (s, $—CH_3$)

B) Preparation of the Compounds of this Invention

EXAMPLE B1

0.085 g (6.94×10$^{-4}$ mol) of dimethylaminopyridine and a large excess of di(2-methyl-3-buten-2-yl)dicarbonate of Example A2 (10 g; 4.1×10$^{-2}$ mol) are added to a suspension of 2 g (6.94×10$^{-3}$ mol) of the pyrrolo[3,4-c]pyrrole of formula

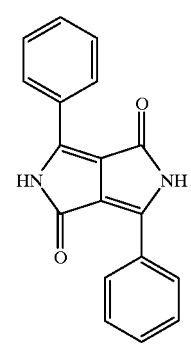

in 50 ml of tetrahydrofuran. The solution is stirred overnight at room temperature and the solvent is then distilled off from the fluorescent orange-brown solution. Hexane is added to the residue, causing the precipitation of an orange solid substance which is then isolated by filtration and dried in the vacuum drying oven, giving 2.39 g (67% of theory) of the compound of formula

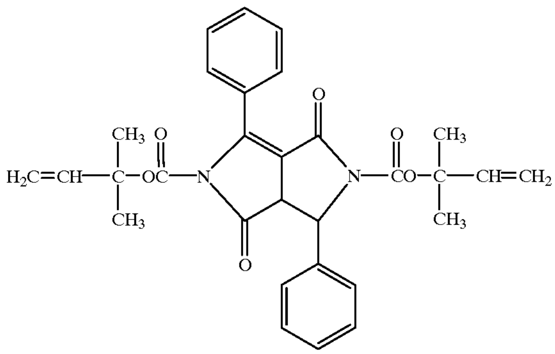

| Analysis: | C | H | N |
|---|---|---|---|
| calcd: | 70.30% | 5.51% | 5.47% |
| found: | 70.30% | 5.57% | 5.38% |

EXAMPLE B2

Example B1 is repeated, with the exception that di(2-methyl-3-buten-2-yl)dicarbonate is replaced with the equivalent amount of di(2-methyl-3-butin-2-yl)dicarbonate of Example A1, giving the compound of formula

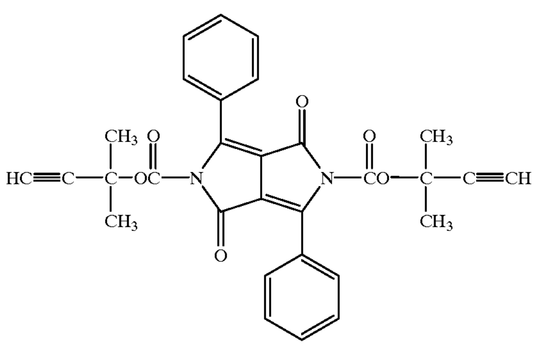

Analysis: $^1$H-NMR ($CD_2Cl_2$): 7.5 (m, 4H); 7.50 (m, 6H); 2.71 (s, 2H); 1.52 (s, 12H)

EXAMPLE B3

Example B1 is repeated, with the exception that di (2-methyl-3-buten-2-yl)dicarbonate is replaced with the equivalent amount of di(3-methyl-2-buten-1-yl)dicarbonate of Example A3, giving the compound of formula

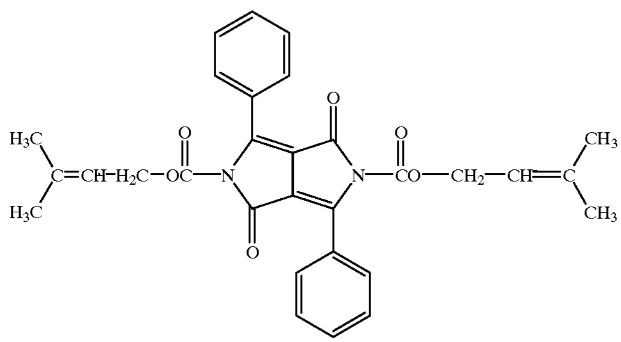

Analysis: $^1$H-NMR ($CD_2Cl_2$): 7.71 (m, 4H); 7.48 (m, 6H); 5.20 (t, 2H); 4.70 (d, 4H); 1.73 (s, 6H); 1.63 (s,1H)

EXAMPLE B4

Example B1 is repeated, with the exception that the pyrrolo[3,4-c]pyrrole is replaced with the equivalent amount of the quinacridone of formula

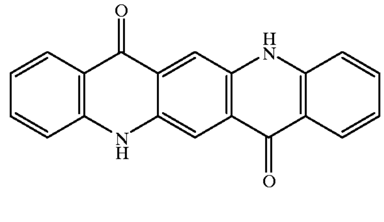
, giving the compound of formula

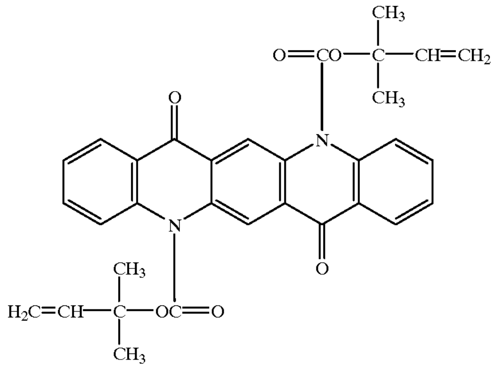

Analysis: $^1$H-NMR ($CD_2Cl_2$): 8.75 (m, 2H); 8.35 (m, 2H); 7.86 (m, 2H); 7.72 (m, 2H); 7.40 (dd, 2H); 6.36 (dd, 2H); 5.43 (d, 2H); 5.32 (d, 2H); 1.77 (s, 6H); 1.76 (s, 6H)

EXAMPLE B5

Example B4 is repeated, with the exception that di(2-methyl-3-buten-2-yl)dicarbonate is replaced with the equivalent amount of di(2-methyl-3-butin-2-yl)dicarbonate, giving the compound of formula

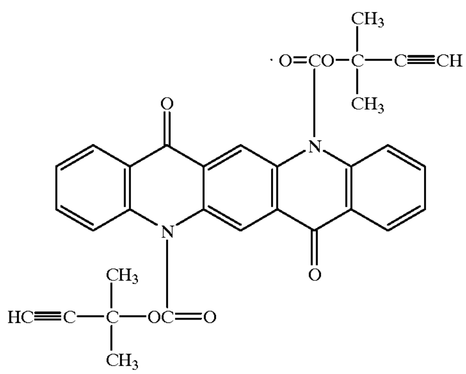

Analysis: $^1$NMR ($CD_2Cl_2$): 8.78 (s, 2H); 8.33 (d, 2H); 7.93 (d, 2H); 7.74 (t, 2H); 7.42 (t, 2H); 2.89 (s,2H); 1.87 (s, 12H)

EXAMPLE B6

0.1 g ($8.2\times10^{-4}$ mol) of dimethylaminopyridine and 1.85 g ($7.6\times10^{-3}$ mol) of di(2-methyl-3-buten-2-yl)dicarbonate are added to a suspension of 1 g ($3.8\times10^{-3}$ mol) of indigo in 40 ml of tetrahydrofuran. After stirring overnight under argon at room temperature, the solution is filtered and the filtrate is then concentrated. Pentane is added to the residue, causing the precipitation of a violet solid substance which is then isolated by filtration and dried in a vacuum drying oven, giving 0.77 g (42% of theory) of the compound of formula

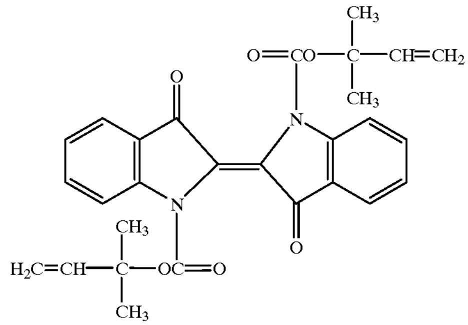

| Analysis: | C | H | N |
|---|---|---|---|
| calcd: | 69.12% | 5.39% | 5.76% |
| found: | 68.65% | 5.64% | 5.68% |

C) Application Examples

By heating the products indicated in the first column of the following Table to the centre temperature indicated under T at a heating rate of 10° C./min, the corresponding pigments (products of the cited formulae, wherein Q' is hydrogen) are reconverted.

| Ex. | Product Q' | Temperature T |
|---|---|---|
| | a) Pyrrolo[3,4-c]pyrroles | |
| | 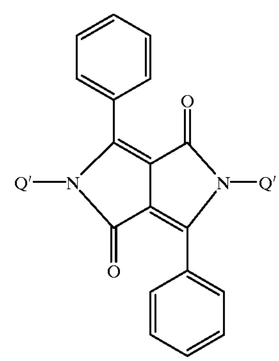 | |
| C1 | 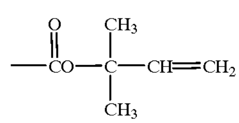 | 125.8° C. |
| C1a | 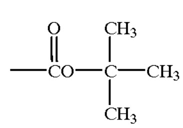 | 177.9° C. |
| | comparison | |
| | b) quinacridones | |

-continued

| Ex. | Product Q' | Temperature T |
|---|---|---|
| | 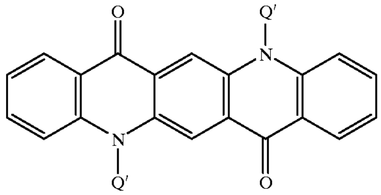 | |
| C2 | 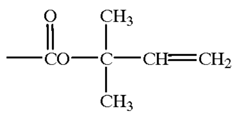 | 124.8° C. |
| C2a | 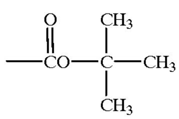 | 185.1° C. |
| | comparison | |
| | C) indigo | |
| | 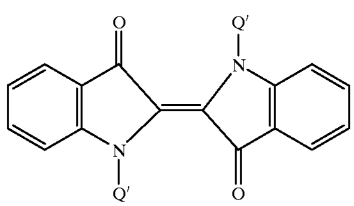 | |
| C3 | 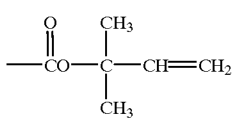 | 165.0° C. |
| C3a | 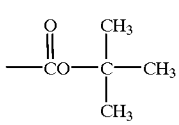 | 197.5° C. |
| | comparison | |

What is claimed is:

1. A compound of formula $$A(B)_x \qquad (I),$$

wherein x is an integer from 1 to 4,

A is the radical of a chromophore of the quinacridone, anthraquinone, perylene, indigo, quinophthalone, isoindolinone, isoindoline, dioxazine, phthalocyanine or azo series, which radical A contains x N-atoms linked to B, B is a group of formula

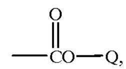

and, if x=2, 3 or 4, can also be one, two or three hydrogen atom(s), and wherein Q is a group of formula

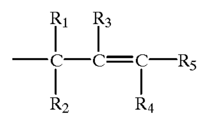 or 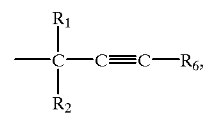

wherein $R_1$ and $R_2$ are each independently of the other hydrogen, $C_1$–$C_{24}$alkyl; $C_1$–$C_{24}$alkyl, $C_3$–$C_{24}$alkenyl, $C_3$–$C_{24}$alkynyl, $C_4$–$C_{12}$cycloalkyl, $C_4$–$C_{12}$cycloalkenyl, each of which is interrupted by O, S or $N(R_9)_2$, phenyl or biphenyl, each of which is unsubstituted or substituted by $C_1$–$C_6$alkyl, $C_1$–$C_6$alkoxy, halogen, cyano or nitro, $R_3$, $R_4$ and $R_5$ are each independently of one another hydrogen, $C_1$–$C_{24}$alkyl or $C_3$–$C_{24}$alkenyl, $R_6$ is hydrogen, $C_1$–$C_{24}$alkyl, $C_3$–$C_{24}$alkenyl or a group of formula

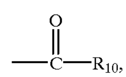 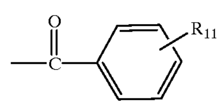 or

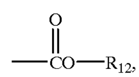

$R_8$ and $R_{10}$ are $C_1$–$C_6$alkyl, $R_{11}$ is hydrogen or $C_1$–$C_6$alkyl, and $R_{12}$ is hydrogen, $C_1$–$C_6$alkyl, unsubstituted or $C_1$–$C_6$alkyl-substituted phenyl, with the proviso that, when A is the radical of a chromophore of a monoazo series, and Q is

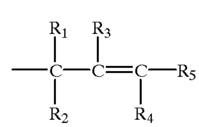

in which $R_1$, $R_2$, $R_3$ and $R_4$ are each hydrogen, the azo group of the monoazo dye is not substituted by 2'-hydroxy-5'-methylphenyl.

2. A compound according to claim 1 of formula I, wherein $R_1$ is $C_1$–$C_{24}$alkyl, $C_3$–$C_{24}$alkenyl, $C_3$–$C_{24}$alkynyl, phenyl which is unsubstituted or substituted by $C_1$–$C_6$alkyl, $C_1$–$C_6$alkoxy, halogen, cyano or nitro, and $R_6$ is $C_1$–$C_{24}$alkyl or $C_3$–$C_{24}$alkenyl.

3. A compound according to claim 1 of formula I, wherein $R_1$ and $R_2$ are methyl, $R_3$, $R_4$ and $R_5$ are each independently of one another hydrogen or $C_1$–$C_{12}$alkyl, and $R_6$ is $C_1$–$C_6$alkyl.

4. A compound according to claim 3 of formula I, wherein B is a group of formula

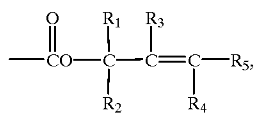

$R_1$ and $R_2$ are methyl, and $R_3$, $R_4$ and $R_5$ are each independently of one another hydrogen or $C_1$–$C_{12}$alkyl.

5. A compound according to claim 1 selected from the group consisting of a) perylenecarboximides of formula (IIa)

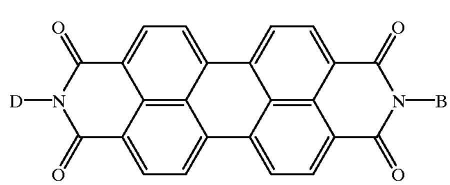

or (IIb)

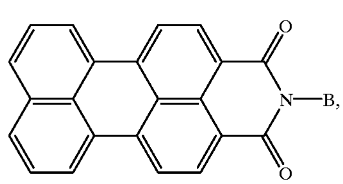

wherein D is hydrogen, $C_1$–$C_6$alkyl; unsubstituted or halogen- or $C_1$–$C_6$alkyl-substituted phenyl, benzyl or phenethyl, or B, b) quinacridones of formula (III)

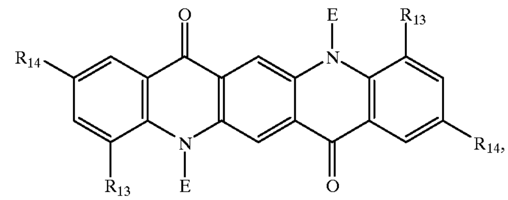

wherein $R_{13}$ and $R_{14}$ are each independently of the other hydrogen, halogen, $C_1$–$C_{24}$alkyl, $C_1$–$C_6$alkoxy or phenyl, c) dioxazines of formula (IV)

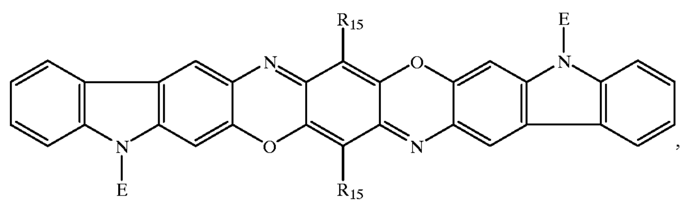

wherein $R_{15}$ is hydrogen, halogen or $C_1$–$C_{24}$alkyl, or of formula (IVa)

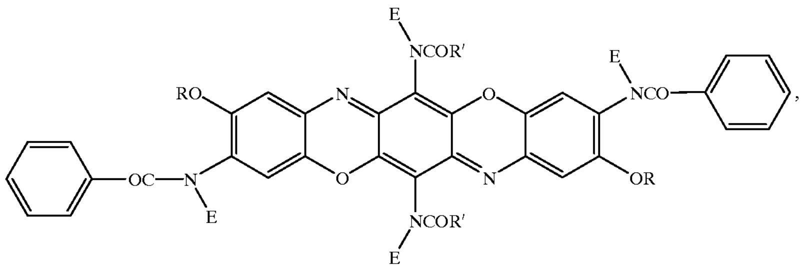

wherein R and R' are each independently of the other $C_1$–$C_4$alkyl, d) isoindolines of formulae (V)

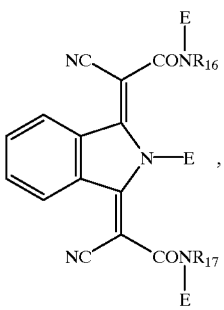

, (VI)

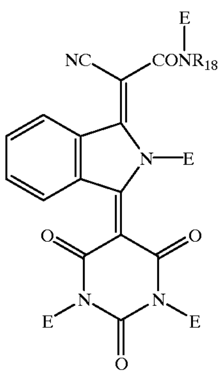

or (VII)

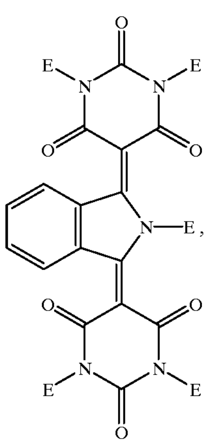

-continued wherein $R_{16}$ is a group of formula

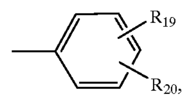

$R_{17}$ is hydrogen, $C_1$–$C_{24}$alkyl, benzyl or a group of formula

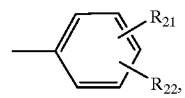

$R_{18}$ has the same meaning as $R_{16}$, $R_{19}$, $R_{20}$, $R_{21}$ and $R_{22}$ are each independently of one another hydrogen, $C_1$–$C_{24}$alkyl, $C_1$–$C_6$alkoxy, halogen or trifluoromethyl, e) indigo derivatives of formula (VIII)

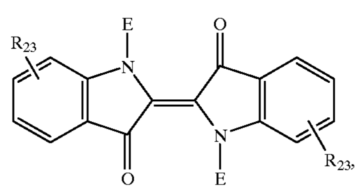

wherein $R_{23}$ is hydrogen, CN, $C_1$–$C_6$alkyl, $C_1$–$C_6$alkoxy or halogen, f) azobenzimidazolones of formula (IX)

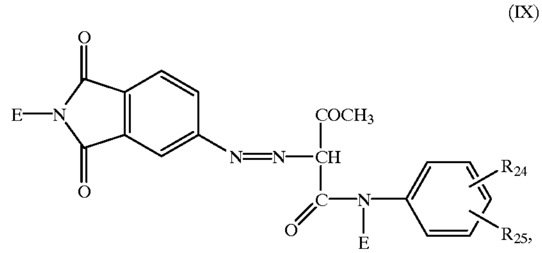

wherein $R_{24}$ and $R_{25}$ are each independently of the other hydrogen, halogen, $C_1$–$C_6$alkyl or $C_1$–$C_6$alkoxy, g) anthraquinoid compounds of formula (X)

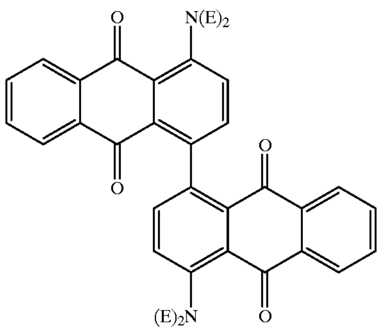

or (XI)

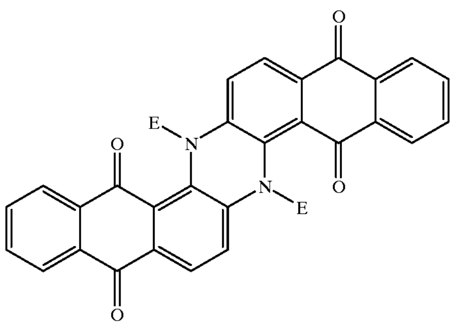

, h) phthalocyanines of formula (XII)

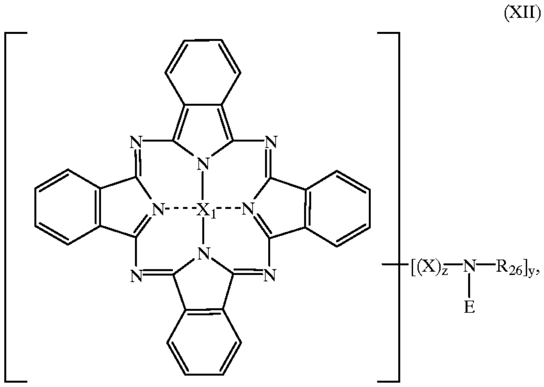

wherein $X_1$ is $H_2$, a divalent metal selected from the group consisting of Cu(II), Zn(II), Fe(II), Ni(II), Ru(II), Rh(II), Pd(II), Pt(II), Mn(II), Mg(II), Be(II), Ca(II), Ba(II), Cd(II), Hg(II), Sn(II), Co(II) and Pb(II), or a divalent oxo metal selected from the group consisting of V(O), Mn(O) and TiO, $X_2$ is —CH($R_{24}$)—, —CO— or —$SO_2$—, $R_{26}$ is hydrogen, $C_1$–$C_6$alkyl, —N(E)$R_{27}$, —NHCO$R_{28}$, —CO$R_{28}$ or

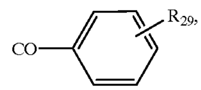

$R_{27}$ is hydrogen or $C_1$–$C_6$alkyl, $R_{28}$ is $C_1$–$C_6$alkyl, and $R_{29}$ is hydrogen, halogen, $C_1$–$C_6$alkyl or $C_1$–$C_6$alkoxy, z is 0 or 1, and y is an integer from 1 to 4, and i) isoindolinones of formula

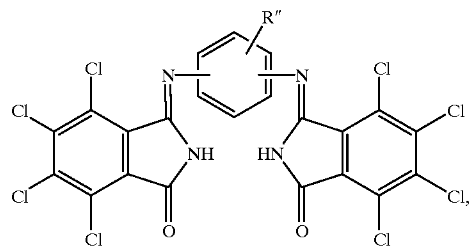

wherein R" is hydrogen or $C_1$–$C_4$alkyl,

E in the above formulae being hydrogen or B, with the proviso that E in each formula is at least once B, and B is as claimed in claim 1.

6. A compound according to claim 5 selected from the group consisting of quinacridones of formula III, wherein $R_{13}$ and $R_{14}$ are each independently of the other hydrogen, chloro or methyl, or anthraquinoid compounds of formula XI wherein E in formulae III and XI is defined as in claim 5.

7. A compound according to claim 4, of formula (XIV)

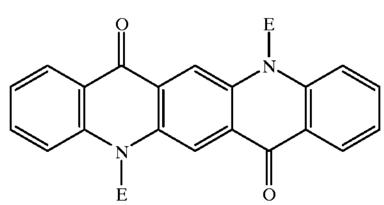

or (XV)

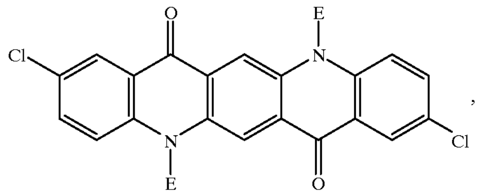

, wherein E is hydrogen or B, with the proviso that E in each formula is at least once B, and B is as claimed in claim 4.

8. A compound according to claim 1 of formula I, wherein the N-atoms linked to B are directly adjacent to or conjugated with at least one carbonyl group.

9. A compound according to claim 4, of formula (XI)

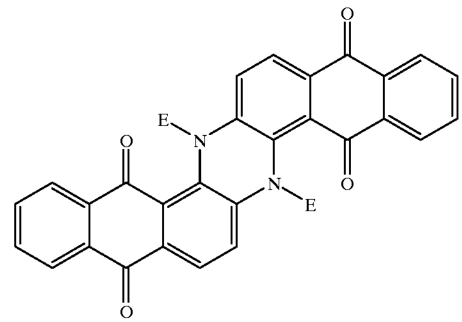

, wherein E is hydrogen or B, with the proviso that E is at least once B, and B is as claimed in claim 4.

* * * * *